United States Patent [19]

Easley et al.

[11] Patent Number: 5,275,593
[45] Date of Patent: Jan. 4, 1994

[54] OPHTHALMIC SURGERY PROBE ASSEMBLY

[75] Inventors: James C. Easley, St. Charles, Mo.; Gholam A. Peyman, New Orleans, La.; Gregory A. Blount, St. Charles; Gregg D. Scheller, Chesterfield, both of Mo.

[73] Assignee: Surgical Technologies, Inc., St. Louis, Mo.

[21] Appl. No.: 876,191

[22] Filed: Apr. 30, 1992

[51] Int. Cl.$^5$ .................................................. A61N 5/02
[52] U.S. Cl. ................................ 606/4; 128/6; 606/16; 604/27
[58] Field of Search ............ 606/4, 3, 2, 13, 14, 606/15, 16, 17; 128/395; 604/38, 27

[56] References Cited

U.S. PATENT DOCUMENTS

| | | | |
|---|---|---|---|
| 4,583,526 | 4/1986 | Ali | 606/3 |
| 4,607,622 | 8/1986 | Fritch et al. | 606/15 |
| 4,784,637 | 11/1988 | Ryder et al. | 604/38 |

Primary Examiner—Stephen C. Pellegrino
Assistant Examiner—Sonja C. Harris
Attorney, Agent, or Firm—Polster, Lieder, Woodruff & Lucchesi

[57] ABSTRACT

An ophthalmic surgery probe assembly includes a handpiece having a handpiece body and a hollow tip of a size suitable for insertion into a human eye, the hollow tip extending distally from the handpiece body. A laser connector is provided for connection to a laser source. A first optical fiber terminates at its proximal end in the laser connector and terminates at the distal end in the handpiece for transmitting laser light from the laser source to an eye to be treated, the first optical fiber extending at least partially through the handpiece tip. An illumination connector is provided for connection to an illumination source. A second optical fiber terminates at its proximal end in the illumination connector and terminates at the distal end in the handpiece for transmitting illumination from the illumination source to an eye to be treated, the second optical fiber extending at least partially through the handpiece tip. The tip also includes a fluid path from the distal end thereof to the interior of the handpiece body. The handpiece body has a fluid path in fluid communication with the fluid path of the tip, the handpiece body fluid path extending to the exterior of the handpiece so that fluid may flow through the tip and the handpiece body while laser light or illumination is directed by the optical fiber into the eye for irrigation and aspiration.

18 Claims, 2 Drawing Sheets

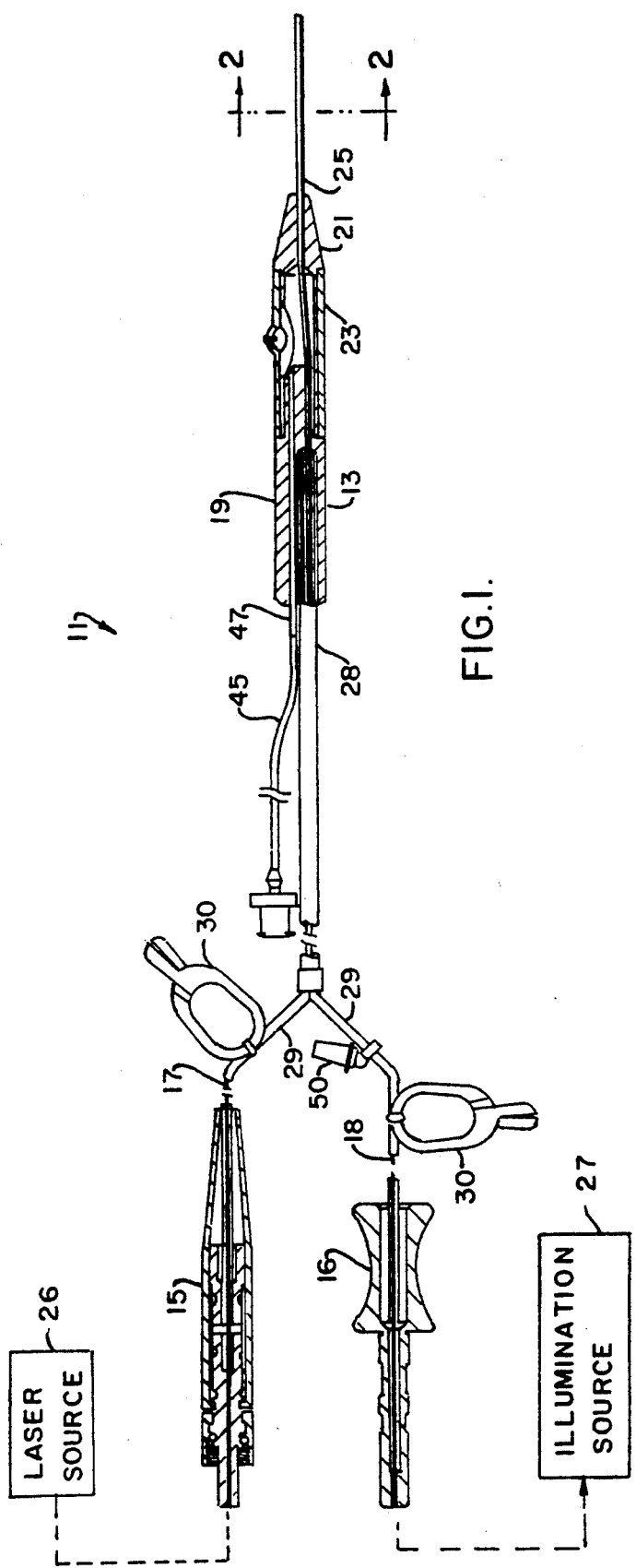
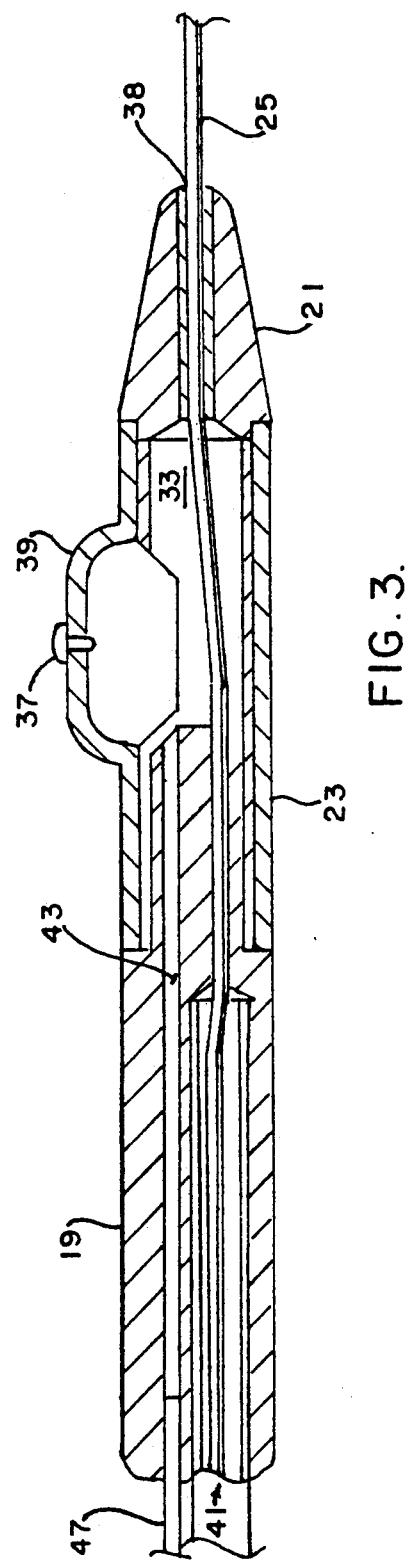

OPHTHALMIC SURGERY PROBE ASSEMBLY

BACKGROUND OF THE INVENTION

The present invention relates to probe assemblies and more particularly to such systems used in ophthalmic surgery and the like.

It is known that ophthalmic surgery involves numerous functions which are typically supplied by separate instruments. For example, separate laser handpieces, illumination probes, and irrigation/aspiration instruments are often used during ophthalmic surgery. Unfortunately, there are disadvantages that result from the use of separate instruments to provide these various functions.

Considering for the moment just laser handpieces and illumination probes, laser light is typically transmitted from a laser source (which is disposed at some distance from the patient) through an optical fiber cable (which can be eight feet or so in length) to the patient. The optical fiber cable terminates proximally in a laser connector (for connection to the laser source) and terminates distally in a handpiece which is manipulated by the surgeon. Similarly, the illumination is transmitted from an illumination source (also disposed at some distance from the patient) through another optical fiber cable to a second handpiece. Use of two separate handpieces requires either separate incisions to accommodate the tips of both handpieces or the successive replacement of one handpiece by the other, which increases the time required for the operation and the resulting trauma to the patient.

In addition, during ophthalmic surgery it is often necessary to remove blood and blood clots from the surface of the retina before the application of laser energy or to irrigate the surface during the time illumination is applied. Currently this is done by using a third instrument (one in addition to the laser handpiece and illumination probe) which has an aspiration/irrigation capability. Given the small incision sizes used in eye surgery, it is often difficult to place the suction probe in the eye simultaneously with the laser probe and an illumination probe because of size limitations, and because the surgeon has only two hands. The laser handpiece must be removed from the eye during suction and replaced when laser treatment is required. This unnecessarily increases the complexity and duration of the medical procedure.

During such medical procedures, the suction probe occasionally draws in material (such as a portion of the retina) which must remain in the eye. Reflux of these materials from current suction probes is not always simple.

These medical procedures presently require at least two hands for operation of the laser handpiece and the suction probe, but both hands are generally not available since one hand is generally occupied with an illumination probe. As a result, the procedures presently require sequential replacement of laser handpiece and suction probe. Reflux of material from the suction probe can require even more hands and/or can significantly increase the complexity of the medical procedure.

There are multi-function instruments for ophthalmic surgery which address some of these problems. For example, instruments are available that provide fiber optic illumination and suction in a single instrument. Such combined-function instruments are desirable since they allow the surgeon to perform multiple functions during the operation without the lost time and trauma otherwise resulting from placing and removing separate instruments.

Present combined-function instruments could, however, be improved. For example, presently available instruments of this type are quite costly and tend to be somewhat unreliable. Moreover, the diameter of these instruments is at the outer margin of what is considered acceptable for instruments which are inserted into the eye.

SUMMARY OF THE INVENTION

Among the several objects and features of the present invention may be noted the provision of an improved probe assembly which is especially suited for ophthalmic surgery or the like.

Another object is the provision of such a probe assembly which provides laser, illumination and aspiration/irrigation capability in a single device.

A third object is the provision of such a probe assembly which provides suction capability precisely at the point where it is needed.

A fourth object is the provision of such a probe assembly which provides laser, illumination and aspiration/irrigation capability in a device operable by one hand.

A fifth object is the provision of such a probe assembly which is reliable, yet relatively simple to manufacture.

Other objects and features will be in part apparent and in part pointed out hereinafter.

Briefly, a probe assembly of the present invention is especially suited for ophthalmic surgery and the like. The probe assembly includes a handpiece having a handpiece body and a hollow tip of a size suitable for insertion into a human eye, the hollow tip extending distally from the handpiece body. A laser connector is included for connection to a laser source with a first optical fiber terminating at the proximal end in the laser connector and terminating at the distal end in the handpiece for transmitting laser light from the laser source to an eye to be treated. The first optical fiber extends at least partially through the handpiece tip. An illumination connector is included for connection to an illumination source, with a second optical fiber terminating at the proximal end in the illumination connector and terminating at the distal end in the handpiece for transmitting illumination from the illumination source to an eye to be treated. The second optical fiber extends at least partially through the handpiece tip, which tip also includes a fluid path from the distal end thereof to the interior of the handpiece body. The handpiece body has a fluid path in fluid communication with the fluid path of the tip, the handpiece body fluid path extending to the exterior of the handpiece so that fluid may flow through the tip and the handpiece body while laser light or illumination is directed by the optical fiber into the eye for irrigation and aspiration.

BRIEF DESCRIPTION OF THE DRAWINGS

FIG. 1 is is a side view, with parts broken away for clarity, of the probe assembly of the present invention;

FIG. 3 is a sectional view, on an enlarged scale, of the handpiece body of the probe assembly of FIG. 1;

Similar reference characters indicate similar parts throughout the several views of the drawings.

DESCRIPTION OF THE PREFERRED EMBODIMENT

Figure 2:
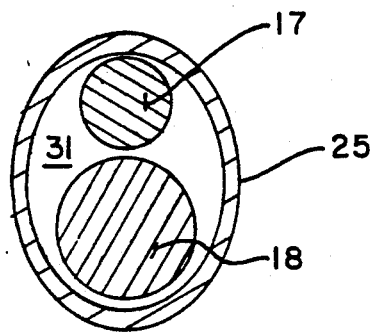
FIG. 2 is an enlarged sectional view taken along lines 2—2 of FIG. 1.

Turning to the drawings, a probe assembly 11 of the present invention includes a handpiece 13, a laser connector 15, an illumination connector 16, and a pair of optical fiber cables 17 and 18. Optical fiber 17, the laser delivery optical fiber, is preferably a glass (silica) optical fiber, while optical fiber 18 (the illumination fiber) may be acrylic or any other suitable material such as other plastics or glass.

Handpiece 13 has a handpiece body made up of a handpiece proximal end portion 19, a handpiece distal end portion 21, and a reflux sleeve 23. A hollow metal tip 25 of a size suitable for insertion into a human eye extends distally from the handpiece body. Tip 25 is preferably a metal tube having approximately one and three-sixteenths inches thereof exposed distally from the handpiece body. The metal tube, although not circular, as explained below, has an outer circumference corresponding to a 20 gauge tube. It is preferred that the wall thickness of the metal tube be as small as possible. These dimensions are illustrative of those for a tip suitable for insertion in the human eye.

Laser connector 15 may be of any desired construction suitable for connection to a laser source 26. The laser connector construction shown is illustrative only.

As can be readily seen in FIG. 1, optical fiber cable 17 terminates proximally in laser connector 15 in such a manner that it is exposed to the laser light from the laser source. The optical cable extends for any desired length (such as eight feet or so) and terminates distally in the tip 25 of handpiece 13. Optical fiber cable 17 thereby forms an optical path for the laser light from the laser source to an eye being treated.

Similarly, illumination connector 16 may be of any desired construction suitable for connection to an illumination source 27. Optical fiber cable 18 terminates proximally in illumination connector 16 so that it is exposed to light from the illumination source. The illumination optical cable also extends for any desired length to terminate distally in the tip 25 of handpiece 13. Optical fiber cable 18 thereby forms an optical path for illumination from the illumination source to an eye being treated.

As can readily be seen from FIG. 1, both optical fibers 17 and 18 are covered by a length of tubing 28 from the handpiece proximally to a separation point where the two fibers separate. From the separation point proximally to the respective connectors, the fibers are covered by individual lengths of tubing 29 all the way back to the respective connectors. Portions of the tubing are removed for clarity in FIG. 1.

Also shown in FIG. 1 are a pair of clamps 30 used to removably secure cables 17 and 18 to any appropriate structure to hold the cables in place without significantly restricting movement of the handpiece by the surgeon. For example, clamps 30 may be readily secured to a surgical drape (not shown) in the operative field by pressing both sides in the directions indicated by the arrows in FIG. 1. This pressure opens the jaws of the clamps so that the jaws may be placed over a fold in the drape. Once the pressure is removed, the jaws close on the drape, thereby holding the respective optical cables fixed in the surgical field. This prevents the optical cables from moving excessively during the medical procedure, which movement could otherwise result in contamination of the sterile field.

Turning to FIG. 2, there is shown on a greatly enlarged scale the relationship between optical fibers 17, 18 and tip 25. The portion of optical fiber 17 which is disposed in tip 25 has an outer diameter of approximately 0.3 mm, for example, while the outer diameter of optical fiber 18 is approximately 0.5 mm. As can readily be seen from FIG. 2, tip 25 has an oval shape which accommodates both optical fibers while reducing the overall size of the tip (compared to a circular tip). Moreover, the placement of the optical fibers leaves a gap 31 disposed between the optical fibers and the inner wall of the tip. This gap runs the entire length of the tip and forms a fluid path from the distal end of tip 25 to the interior of the handpiece body.

Note that if the optical fibers were secured to tip 25 by adhesive, the adhesive would tend to block off gap 31. To prevent this, the optical fibers are not secured directly to tip 25 at all. Instead they are suitably secured to proximal end portion 19 of the handpiece body.

The fluid path formed by gap 31 allows fluid and other material to be withdrawn through the gap and also permits irrigation of the operative area as desired. Significantly, the distal end of this fluid path is disposed immediately adjacent the spot where the laser light and illumination exit the tip, so that aspiration and irrigation takes place almost exactly where needed.

The fluid path formed by gap 31 is in fluid communication with a fluid path through handpiece 13. That latter fluid path is formed by a cavity 33 (FIG. 3) formed in handpiece distal end portion 21, which opens into a cavity 35 between handpiece distal end portion 21 and reflux sleeve 23. Sleeve 23 has a port 36 (shown plugged by a stainless steel plug 37 in FIG. 3) formed therein above cavity 35, so that fluid in cavity 35 may flow out the port to the exterior of handpiece 13 when plug 37 is not present.

As is known, the interior of an eye being operated on may be placed under pressure with a suitable solution so as to maintain its sphericity during the procedure. This pressure causes fluid to flow through gap 31 in handpiece tip 25, through cavities 33 and 35, and out the port. The surgeon can stop this flow simply by covering port 37 with a finger.

Note that with this construction, fluid in the eye may flow through the tip and the handpiece body even while laser light from the laser source or illumination from the illumination source are directed by the optical fibers into the eye. The surgeon, with one-handed control, can thus apply laser power or illumination to the surgical area while at the same time aspirating or irrigating exactly the same area.

Also shown in FIG. 3 is a bushing 38 in which is mounted tip 25. Bushing 38 is preferably stainless steel and is itself suitably secured to distal handpiece portion 21.

On occasion, distal tip 25 can suction in undesired material, such as a portion of the retina. With the present construction, this material can easily and rapidly be refluxed back into the eye, again with a one-handed operation. Reflux sleeve 23 is formed from a relatively soft, elastically deformable, resilient material such as 50 durometer silicone rubber.

Figure 4:
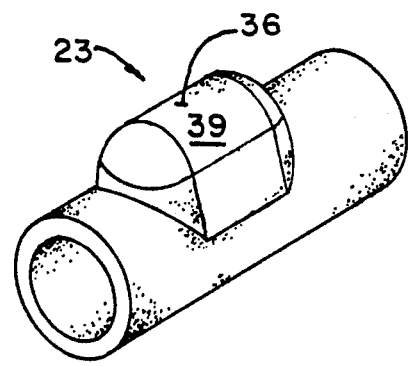
FIG. 4 is a perspective view of a reflux sleeve making up a portion of the probe assembly of FIG. 1.
Figure 4A:
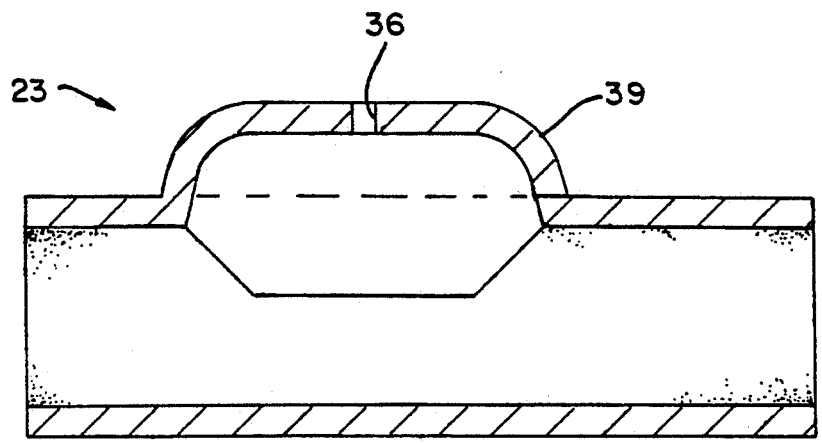
FIG. 4A is a cross-sectional view of the reflux sleeve of FIG. 4, on an enlarged scale.

Sleeve 23 is shown best in FIGS. 4 and 4A. It includes an elongate bulb 39 located directly over cavity 35 (which cavity is formed by cutting away the corresponding part of handpiece distal end portion 21). By pressing downwardly on bulb 39 above cavity 35, the surgeon applies pressure on the fluid path through the distal end of tip 25. This pressure forces any undesired material back out of the distal end of tip 25. Note that because port 36 is disposed on bulb 39, the mere act of pressing downwardly on the sleeve in this location automatically closes port 36. This ensures that the effect of the downward motion is to force fluid and any accompanying material distally out of tip 25.

Turning back to FIG. 3, the proximal portion 19 of the handpiece has a first bore 41 through which passes optical fiber 17, and a second bore 43 in fluid communication with cavities 33 and 35. Bore 43 may be attached to any suitable aspiration/irrigation source by means of a conventional tube 45 (see FIGS. 1, 5, and 6) fixedly secured in a sleeve 47 disposed in bore 43. A syringe 48 (FIG. 5) for example constitutes a suitable aspiration/irrigation source.

Figure 5:
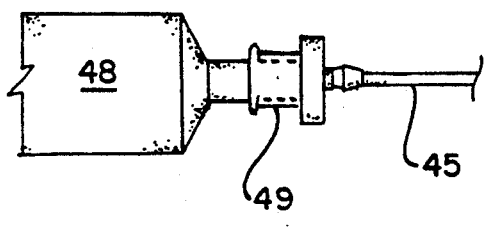
FIG. 5 is a partial elevation of the probe assembly of FIG. 1 attached to an aspiration/irrigation source.
Figure 6:
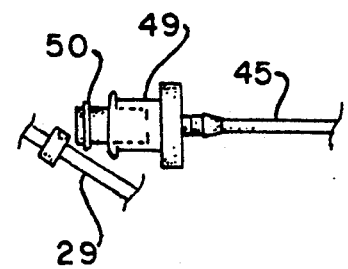
FIG. 6 is a partial elevation of the probe assembly of FIG. 1 with the aspiration/irrigation port thereof closed by a plug.

As can be seen in FIGS. 1, 5, and 6, tube 45 terminates proximally in a suitable connector 49 adapted to accept the aspiration/irrigation source. A plug 50 is provided to close off connector 49 when not in use (see FIG. 6). Plug 50 is suitably connected to tubing 29 so that it cannot be lost.

In view of the above it will be seen that the various objects and features of the above described invention are achieved and other advantageous results obtained. The description and drawings of the present invention contained herein are illustrative only and are not to be interpreted in a limiting sense.

What is claimed is:

1. A probe assembly for opthalmic surgery and the like comprising:
    a handpiece having a handpiece body and a hollow tip of a size suitable for insertion into a human eye, said handpiece body having a proximal end and a distal end, said hollow tip having a proximal end and a distal end and extending distally from the handpiece body;
    a laser connector for connection to a laser source;
    a first optical fiber having a proximal end and a distal end, said first optical fiber terminating at the proximal end in the laser connector and terminating at the distal end in the handpiece for transmitting laser light from the laser source to an eye to be treated;
    said first optical fiber extending at least partially through the handpiece tip;
    an illumination connector for connection to an illumination source;
    a second optical fiber having a proximal end and a distal end, said second optical fiber terminating at the proximal end in the illumination connector and terminating at the distal end in the handpiece for transmitting illumination from the illumination source to an eye to be treated;
    said second optical fiber extending at least partially through the handpiece tip;
    said tip also including a fluid path from the distal end thereof to the interior of the handpiece body;
    said handpiece body having a fluid path in fluid communication with the fluid path of the tip, said handpiece body fluid path extending to the exterior of the handpiece, whereby fluid may flow through the tip and the handpiece body while laser light or illumination is directed by the optical fiber into the eye for irrigation and aspiration.

2. The probe assembly as set forth in claim 1 wherein the handpiece body fluid path includes a cavity inside the handpiece body, a bore extending from the cavity to the exterior of the handpiece, and a tube for providing fluid communication between the bore and an irrigation/aspiration source, said tube having a proximal end and a distal end.

3. The probe assembly as set forth in claim 2 further including a plug for plugging the proximal end of the fluid communication tube, said plug being secured to the probe assembly at a position convenient to the proximal end of the fluid communication tube.

4. The probe assembly as set forth in claim 2 wherein the irrigation/aspiration source is a syringe, said fluid communication tube terminating at its proximal end in a fitting suitable for accepting the distal end of the syringe.

5. The probe assembly as set forth in claim 2 further including a sleeve disposed around the distal end of the fluid communication tube at the handpiece.

6. The probe assembly as set forth in claim 1 wherein the handpiece tip is substantially non-circular in cross section.

7. The probe assembly as set forth in claim 6 wherein the handpiece tip is substantially oval in cross section.

8. The probe assembly as set forth in claim 6 wherein the first optical fiber and the second optical fiber extend substantially to the distal end of the handpiece tip.

9. The probe assembly as set forth in claim 6 wherein the first optical fiber is substantially smaller in diameter than the second optical fiber.

10. The probe assembly as set forth in claim 6 wherein the interior cross-sectional area of the handpiece tip is larger than the sum of the cross-sectional areas of the first and second optical fibers.

11. The probe assembly as set forth in claim 1 further including a bushing disposed in the distal end of the handpiece body, said hollow tip being secured in said bushing.

12. The probe assembly as set forth in claim 1 further including a length of tubing covering the first and second optical fibers for a predetermined distance proximally from the proximal end of the handpiece.

13. The probe assembly as set forth in claim 12 further including first and second separate lengths of tubing covering the first and second optical fibers respectively proximally from the aforesaid length of tubing to the laser and illumination connectors.

14. The probe assembly as set forth in claim 1 wherein the sum of the first optical fiber diameter and the second optical fiber diameter substantially equal the inner dimension of the handpiece tip measured along the major axis of the tip.

15. The probe assembly as set forth in claim 1 wherein the inner dimension of the handpiece tip measured along the minor axis of the tip is substantially less than the inner dimension measured along the major axis of the tip.

16. The probe assembly as set forth in claim 1 wherein the first optical fiber is composed of a different material than the second optical fiber.

17. The probe assembly as set forth in claim 16 wherein the first optical fiber is silica.

18. The probe assembly as set forth in claim 1 wherein the handpiece tip substantially corresponds in outer circumference to twenty gauge tubing.

* * * * *